United States Patent [19]

Nedelec et al.

[11] 4,263,290
[45] Apr. 21, 1981

[54] NOVEL 19-NOR-STEROIDS

[75] Inventors: Lucien Nedelec, Le Raincy; Vesperto Torelli, Maisons-Alfort; Robert Fournex, Paris, all of France

[73] Assignee: Roussel Uclaf, Romainville, France

[21] Appl. No.: 98,766

[22] Filed: Nov. 30, 1979

[30] Foreign Application Priority Data

Dec. 13, 1978 [FR] France .................. 78 35046

[51] Int. Cl.³ .......................... A61K 31/56; C07J 5/00
[52] U.S. Cl. ........................... 424/243; 260/239.55 R; 260/397.47; 260/397.3; 260/397.4; 260/340.9 AS
[58] Field of Search .................. 424/243; 260/397.47, 260/340.9 AS, 239.55, 397.3, 397.4

[56] References Cited

U.S. PATENT DOCUMENTS 4,136,179  1/1979  Nedelec et al. ............. 260/239.55 C Primary Examiner—Elbert L. Roberts
Attorney, Agent, or Firm—Hammond & Littell, Weissenberger and Muserlian

[57] ABSTRACT

Novel 19-nor-steroids of the formula

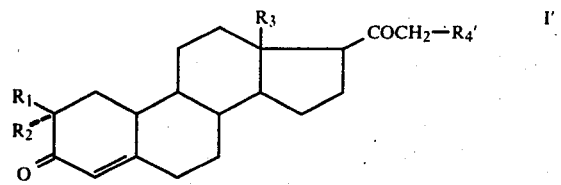

wherein $R_1$ and $R_2$ taken together form a cycloalkyl of 3 to 8 carbon atoms or are individually selected from the group consisting of hydrogen, alkyl of 1 to 4 carbon atoms and alkenyl and alkynyl of 2 to 6 carbon atoms with the proviso that both cannot be hydrogen, $R_3$ is alkyl of 2 to 4 carbon atoms, $R_4'$ is selected from the group consisting of hydrogen, hydroxyl, acyloxy of an organic carboxylic acid of 1 to 18 carbon atoms and

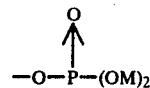

and M is selected from the group consisting of hydrogen and alkali metal, having antagonistic properties to aldosterone and increasing sodium-water diuresis with conservation of organic potassium and a novel process and novel intermediates for their preparation.

33 Claims, No Drawings

NOVEL 19-NOR-STEROIDS

STATE OF THE ART

Related compounds are described in commonly assigned U.S. Pat. Nos. 4,078,059 and No. 4,136,179.

OBJECTS OF THE INVENTION

It is an object of the invention to provide the novel 19-nor-steroids of formula I' as well as a novel process and novel intermediates for the preparation thereof.

It is another object of the invention to provide novel aldosterone antagonistic compositions and to a novel process for inducing increased sodium-water diuresis and organic potassium conservation without side effects.

These and other objects and advantages of the invention will become obvious from the following detailed description.

THE INVENTION

The novel 19-nor-$\Delta^4$-3-one steroids of the invention have the formula

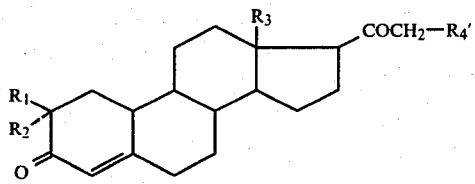

wherein $R_1$ and $R_2$ taken together form a cycloalkyl of 3 to 8 carbon atoms or are individually selected from the group consisting of hydrogen, alkyl of 1 to 4 carbon atoms and alkenyl and alkynyl of 2 to 6 carbon atoms with the proviso that both cannot be hydrogen, $R_3$ is alkyl of 2 to 4 carbon atoms, $R_4'$ is selected from the group consisting of hydrogen, hydroxyl, acyloxy of an organic carboxylic acid of 1 to 18 carbon atoms and

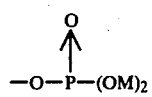

and M is selected from the group consisting of hydrogen and alkali metal. Particularly preferred are the compounds wherein $R_4'$ is selected from the group consisting of hydrogen, —OH and acyloxy of an organic carboxylic acid of 1 to 18 carbon atoms.

Examples of suitable carboxylic acids of 1 to 18 carbon atoms for the acyloxy group are saturated or unsaturated aliphatic or cycloaliphatic carboxylic acids such as alkanoic acids like acetic acids, propionic acids, butyric acid, isobutyric acid and undecylic acid; cycloalkylcarboxylic acids like cyclopropylcarboxylic acid, cyclopentylcarboxylic acid and cyclohexylcarboxylic acid; cycloalkanoic acids like cyclopentylacetic acid, cyclopentylpropionic acid, cyclohexylacetic acid and cyclohexylpropionic acid; aryl carboxylic acids such as benzoic acid, m-sulfobenzoic acid and phenylalkanoic acids such as phenylacetic acid or phenylpropionic acid.

The acyloxy group may also have the formula

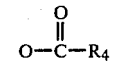

wherein $R_4$ contains at least one heteroatom selected from the group consisting of nitrogen, oxygen and sulfur or is a hydrocarbon chain containing at least one oxygen atom. Examples of

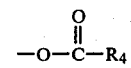

are those wherein $R_4$ is selected from the group consisting of 3-pyridinyl, 4-pyridinyl, thiazolyl, 4,5-dihydrothiazolyl, oxazolyl and imidazolyl. $R_4$ may also be the group $AlK_1-[(CH_2)_n-O]_m-AlK_2$ wherein n is a number from 1 to 8, m is a number from 1 to 6 and $AlK_1$ and $AlK_2$ are individually saturated or unsaturated, linear or branched alkyl of 1 to 8 carbon atoms or $(CH_2)_p$—COOH and p is a number from 1 to 8.

Examples of $R_1$ and $R_2$ are alkyl of 1 to 4 carbon atoms such as methyl, ethyl, alkenyl of 2 to 6 carbon atoms such as allyl, alkynyl of 2 to 6 carbon atoms such as ethynyl, preferably 2-propynyl and hydrogen or taken together form a cycloalkyl of 3 to 8 carbon atoms such as cyclopropyl, cyclobutyl, cyclopentyl or cyclohexyl.

Preferred compounds of formula I' are those wherein $R_1$ and $R_2$ are methyl and $R_3$ is ethyl.

Especially preferred of the invention are those of the formula

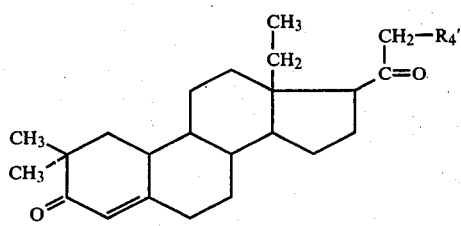

wherein $R_4''$ is selected from the group consisting of hydrogen, hydroxyl and acyloxy of an organic carboxylic acid of 1 to 18 carbon atoms.

Among the preferred compounds of formula I' are those wherein $R_4'$ is hydrogen, hydroxy, acetoxy or 4-pyridinylcarbonyloxy.

Examples of specific preferred compounds of formula I' are 2,2-dimethyl-13$\beta$-ethyl-18,19-dinor-$\Delta^4$-pregnene-21-ol-3, 20-dione, 21-disodium monophosphate of 2,2-dimethyl-13$\beta$-ethyl-18,19-dinor-$\Delta^4$-pregnene-21-ol-3,20-dione, 2-allyl-13$\beta$-ethyl-18,19-dinor-$\Delta^4$-pregnene-3,20-dione, 2-allyl-13$\beta$-ethyl-18,19-dinor-21-acetoxy-$\Delta^4$-pregnene-3,20-dione, 2-allyl-13$\beta$-ethyl-18,19-dinor-$\Delta^4$-pregnene-21-ol-3,20-dione, 2$\alpha$-and 2$\beta$-methyl-13$\beta$-ethyl-18,19-dinor-$\Delta^4$-pregnene-3,20-dione, 2$\alpha$-methyl-13$\beta$-ethyl-18,19-dinor-21-acetoxy-$\Delta^4$-pregnene-3,20-dione, 2$\beta$-methyl-13$\beta$-ethyl-18,19-dinor-21-acetoxy-$\Delta^4$-pregnene-3,20-dione, 2$\alpha$- and 2$\beta$-methyl-13$\beta$-ethyl-18,19-dinor-$\Delta^4$-pregnene-21-ol-3, 20-dione, 2$\alpha$- and 2$\beta$-propyl-13$\beta$-ethyl-18,19-dinor-$\Delta^4$-pregnene-3,20-dione, 2$\alpha$-propyl-13$\beta$-ethyl-18,19-dinor-21-acetoxy-$\Delta^4$-pregnene-3,20-dione, 2$\beta$-propyl-13$\beta$-ethyl-18,19-dinor-21-acetoxy-$\Delta^4$-pregnene-3,20-dione, 2$\alpha$- and 2$\beta$-propyl-13$\beta$-ethyl-18,19-dinor-$\Delta^4$-pregnene-21-ol-3,20-dione, 2,2-diethyl-13$\beta$-ethyl-18,19-dinor-$\Delta^4$-pregnene-3,20- dione, 2,2-diethyl-13β-ethyl-18,19-dinor-21-acetoxy-Δ⁴-pregnene-3,20-dione and 2,2-diethyl-13β-ethyl-18,19-dinor-Δ⁴-pregnene-21-ol-3,20-dione.

The novel process of the invention for the preparations of the compounds of formula I' comprises using the Wittig reaction by reacting a compound of the formula

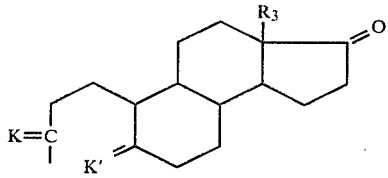

wherein K and K' are ketone blocking ketal groups and R₃ is alkyl of 2 to 4 carbon atoms with a triphenyl ethyl phosphonium halide of the formula

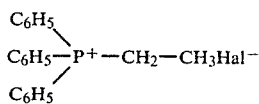

wherein Hal is a halogen in the presence of a strong base to form a compound of the formula

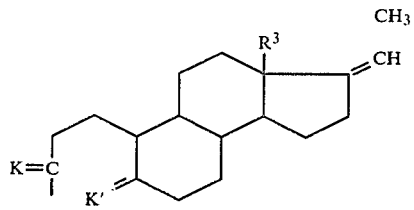

in the form of its cis and trans isomers, optionally separating the said isomers, reacting the compound in the form of its isomer or mixtures thereof with a hydroboration agent, then with an oxidation agent in an alkaline medium, then with a deketalization agent and finally a cyclization agent to obtain a compound of the formula

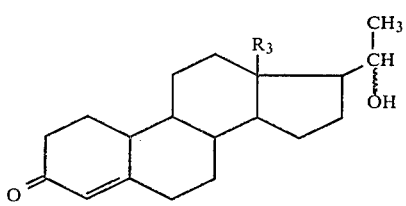

in the form of its 20R or 20S isomers or a mixture thereof, reacting the compound of formula V with an alcohol blocking agent to obtain a compound of the formula

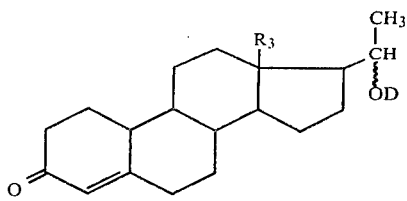

in the form of its 20R or 20S isomer or a mixture thereof and OD is an ether group, reacting the compound of formula VI with an alkyl halide, alkenyl halide or alkynyl halide in the presence of a basic agent at low temperatures to obtain a compound of the formula

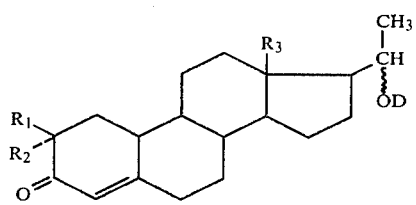

wherein R₁ and R₂ have the above definition in the form of its 20R or 20S isomer or a mixture thereof, reacting the compound of formula VII with a hydrolysis agent and then an oxidation agent to obtain a compound of the formula

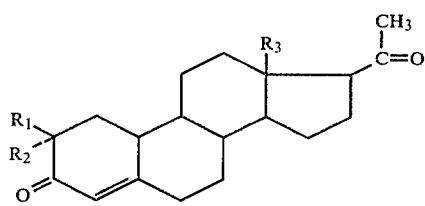

optionally reacting the latter with lead tetraacetate or with an oxylation agent and then a halogenation agent to form the corresponding 21-halo compound and reacting the latter with an acetoxylation agent to obtain a compound of the formula optionally reacting the latter with a saponification agent to obtain a compound of the formula optionally reacting the latter with an organic carboxylic acid of 1 to 18 carbon atoms or a functional derivative thereof to obtain a compound of the formula

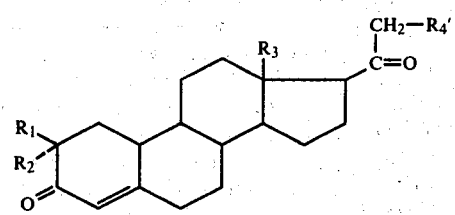

wherein $R_4'$ is an acyloxy of an organic carboxylic acid of 1 to 18 carbon atoms or with a functional derivative of phosphoric acid to obtain the compound of formula $I_D$ wherein $R_4'$ is

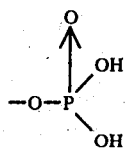

which may be salified, if desired.

In a preferred embodiment of the said process, $R_3$ is ethyl and K and K' are cyclic alkylketals of 2 to 4 carbon atoms such as ethylene ketal or propylene ketal or dialkylketals of 1 to 4 alkyl groups such as dimethylketal or diethylketal.

The Wittig reaction conditions are described in Organic Reactions, Vol. 14 (1965), p. 270 and the halide reactant is preferably triphenyl ethyl phosphonium bromide. The strong base is preferably an alkali metal alcoholate such as sodium tert.-amylate, potassium tert.-amylate, sodium tert.-butylate or potassium tert.-butylate and the reaction is effected in an organic solvent such as benzene, toluene, tetrahydrofuran, dioxane or dimethylsulfoxide.

The hydratation of olefins of formula IV is realized by the method of Brown described in Organic Reactions, Vol. 13 (1963), p. 1. The hydroboration agent may be diborane or diborane formed in situ by reaction of sodium borohydride and boron trifluoride or with a dialkylborane such as diisoamylborane or 9-bora-bicyclo-[3,3-1]-nonane. The oxidation agent in an alkaline media is preferably hydrogen peroxide in sodium hydroxide or potassium hydroxide solution. Preferably, a single reactant is used as the deketalization agent and cyclization agent and is a strong acid such as sulfuric acid or hydrochloric acid. However, 2 separate agents may be used such as a weak acid like acetic acid for the deketalization step and a basic agent such as sodium hydroxide or potassium hydroxide for the cyclization.

The various isomers at the 20-position may be separated by classical methods such as crystallization or chromatography. The preferred alcohol blocking agent is dihydropyran.

Preferably, $R_1$ and $R_2$ are both methyl and the gem-dimethylation is effected with methyl iodide in the presence of an alkali metal alcoholate such as potassium tert.-butylate. Preferably, an aprotic solvent such as tetrahydrofuran is used for the gem-dimethylation step. The hydrolysis agent used with the compound of formula VII is preferably an acid such as hydrochloric acid, sulfuric acid, acetic acid or p-toluene sulfonic acid. The oxidation agent next used is a Heilbron-Jones reactant, namely chromic acid anhydride dissolved in dilute sulfuric acid.

The reaction with lead tetraacetate is preferably effected in the presence of boron trifluoride-etherate. The preferred oxalylation agent is ethyl oxalate and the preferred halogenation agent is preferably iodine or bromine. The preferred acetoxylation agent is potassium acetate. The preferred saponification agent is an alkali metal base such as sodium hydroxide, potassium hydroxide, potassium carbonate or potassium bicarbonate and the reaction is effected in a lower alkanol such as methanol or ethanol.

The preferred acid functional derivative is the acid anhydride or the acid halide such as as its chloride or bromide. The phosphorus derivative may be prepared by classical methods and the salification may be effected with sodium hydroxide or potassium hydroxide for example.

The novel intermediate products of the invention are the compounds of formulae IV, V, VI and VII.

The starting compounds of formula II are generally known compounds and may be prepared by the process of French Pat. No. 1,490,590 and Danish Pat. No. 136,115.

The novel compositions of the invention have aldosterone antagonistic properties, they increase water-sodium diuresis with conservation of organic potassium and are without side effects. They are comprised of an effective amount of at least one compound of formula I' and an inert pharmaceutical carrier or excipient. The compositions may be in the form of tablets, dragees, cachets, capsules, granules, emulsions, syrups, suppositories and injectable solutions and suspensions.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants and emulsifiers or preservatives.

The compositions are useful as antialdosterone agents and do not show antiestrogenic or antiandrogenic activity. They are useful for the treatment of arterial hypertension and cardiac insuffficiences.

The novel method of the invention of treating arterial hypertension and cardiac insufficiency in warm-blooded animals, including humans, comprises administering to warm-blooded animals an amount of at least one compound of formula I' sufficient to relieve arterial hypertension and cardiac insufficiency. The compounds may be administered orally, rectally, transuctaneously or intraveinously. The usual useful daily dosage is depending on the compound and the method of treatment and may be 0.2 to 0.02 mg/kg of oral route.

In the following examples there are described several preferred embodiments to illustrate the invention. However, it should be understood that the invention is not intended to be limited to the specific embodiments.

EXAMPLE 1

2,2-dimethyl-13β-ethyl-18,19-dinor-Δ⁴-pregnene-3,20-dione

STEP A: Mixture of Z and E isomers of bis-(1,2-ethanediyl)-cyclic acetal of 13β-ethyl-18,19-dinor-4,5-seco-Δ$^{17(20)}$-pregnene-3,5-dione 27.2 g of bis-(1,2-ethanediyl)-cyclic acetal of 13β-ethyl-18,19-dinor-4,5-seco-androstane-17-one were added to a mixture of 51.2 g of triphenyl ethylphosphonium bromide and 136 ml of dimethylsulfoxide containing 16.8 g of potassium tert.-butylate and the mixture was heated to 50° C. with stirring under a nitrogen current for 65 hours. The mixture was poured into 1.5 liters of water and the mixture was extracted with ether. The combined organic phases were washed with water, dried and evaporated under reduced pressure to a small volume and then was filtered to remove triphenylphosphonium oxide. The filtrate was evaporated to dryness and the residue was chromatographed over silica gel. Elution with an 8-2 cyclohexane-ethyl acetate mixture yielded 27.35 g of mixture of Z and E isomers of bis-(1,2-ethanediyl)-cyclic acetal of 13$\beta$-ethyl-18,19-dinor-4,5-seco-$\Delta^{17(20)}$-pregnene-3,5-dione which was used as is for the next step.

STEP B: 13$\beta$-ethyl-20-(R,S)-hydroxy-18,19-dinor-$\Delta^4$-pregnene-3-one

A solution of 6.25 ml of boron trifluoride-etherate in 19 ml of anhydrous tetrahydrofuran was added under nitrogen to a suspension of 1.9 g of sodium borohydride in 19 ml of anhydrous tetrahydrofuran at $-10°$ to $-15°$ C. and the suspension was stirred for one hour at $-5°$ C. Then, a solution of 10 g of the product of Step A in 30 ml of tetrahydrofuran was added to the mixture over 10 minutes and the reaction mixture was allowed to return to room temperature where it was stirred for 90 minutes. The mixture was cooled to $-10°$ C. and 30 ml of sodium hydroxide solution followed by 30 ml of water were very slowly added thereto. The decanted organic phase was washed twice with 3 N sodium hydroxide and then was added to 100 ml of 3 N sodium hydroxide solution. The two phases were emulsified by stirring and then 50 ml of 33% perhydroxide were slowly added thereto at room temperature. The resulting mixture was stirred for 45 minutes and the decanted aqueous phase was extracted with ethyl acetate. The combined organic phases were washed with a 10% sodium thiosulfate solution and dried and evaporated to dryness under reduced pressure. The residue was added to 100 ml of ethanol and 50 ml of 5 N hydrochloric acid. The resulting solution was refluxed for 50 minutes and was then diluted with water. The mixture was extracted with chloroform and the organic phase was washed with water, dried and evaporated to dryness under reduced pressure. The 9.8 g of residue were crystallized from isopropyl ether to obtain 5.1 g of 13$\beta$-ethyl-20-(R,S)-hydroxy-18,19-dinor-$\Delta^4$-pregnene-3-one which melted at 140° C. After crystallization from aqueous methanol, the product melted at 142° C. The product was chromatographed over silica gel and was eluted with a 1-1 cyclohexane-ethyl acetate mixture to obtain the 20R isomer melting at 150° C. and the 20S isomer melting at 169° C.

STEP C: 13$\beta$-ethyl-(2'RS, 20RS)-20-[2'-tetrahydropyranyloxy]-18,19-dinor-$\Delta^4$-pregnene-3-one 135 mg of p-toluene sulfonic acid were added to a solution of 13.42 g of the 20 (R,S) compound of Step B in 135 ml of anhydrous benzene and 27 ml of dihydropyran and the mixture stood at room temperature for one hour. 1 ml of triethylamine was added thereto and the organic phase was washed with water, dried and evaporated to dryness under reduced pressure to obtain 19.1 g of crystalline 13$\beta$-ethyl-(2'RS, 20RS)-20-[2'-tetrahydropyranyloxy]-18,19-dinor-$\Delta^4$-pregnene-3-one which was used as is for the next step.

STEP D: (2'RS, 20RS) 2,2-dimethyl-13$\beta$-ethyl-20-[2'-tetrahydropyranyloxy]-18,19-dinor-$\Delta^4$-pregnene-3-one A solution of 9.2 g of potassium teert.-butylate in 45 ml of anhydrous tetrahydrofuran was added under a nitrogen atmosphere over 20 minutes to a solution of 6.6 g of the product of Step C in 50 ml of anhydrous tetrahydrofuran and 11 ml of methyl iodide cooled to $-65°$ C. and the mixture was stirred at $-65°$ C. for 30 minutes. The mixture was diluted with water and was then extracted with chloroform. The organic phase was washed with water, dried and evaporated to dryness under reduced pressure to obtain 7.1 g of residue containing (2'RS, 20RS) 2,2-dimethyl-13$\beta$-ethyl-20-[2'-tetrahydropyranyloxy]-18,19-dinor-$\Delta^4$-pregnene-3-one which was used as is for the next step.

STEP E: 2,2-dimethyl-13$\beta$-ethyl-18,19-dinor-$\Delta^4$-pregnene-3,20-dione

A solution of 7.1 g of the product of Step D, 70 ml of ethanol and 14 ml of 2 N hydrochloric acid was refluxed for one hour and was diluted with water. The mixture was extracted with methylene chloride and the organic phase was evaporated to dryness. The 6.9 g of residue was dissolved in 200 ml of acetone which was cooled to 0° to $-5°$ C. Then, 5 ml of Heilbron-Jones reactant were added thereto over 15 minutes and the mixture was stirred for 15 minutes at 0° to $-5°$ C. Excess reactant was destroyed by the addition of methanol and the mixture was diluted with water and was extracted with methylene chloride. The organic phase was evaporated to dryness and the 5.9 g of residue was chromatographed over silica gel. Elution with an 85-15 cyclohexane-ethyl acetate mixture yielded 2.6 g of 2,2-dimethyl-13$\beta$-ethyl-18,19-dinor-$\Delta^4$-pregnene-3,20-dione melting at 179° C. after crystallization from a methylene chloride-isopropyl ether mixture.

EXAMPLE 2

2,2-dimethyl-13$\beta$-ethyl-21-acetoxy-18,19-dinor-$\Delta^4$-pregnene-3,20-dione 450 mg of sodium borohydride as a 50% mineral oil dispersion were added to a solution of 1.920 g of the product of Example 1 in 20 ml of anhydrous benzene and 2 ml of ethyl oxalate and then one drop of ethanol was added to start the reaction. The suspension was stirred for 50 minutes until hydrogen evolution ceased and was acidified with a solution of gaseous hydrochloric acid in ethyl acetate. The mixture was filtered to remove mineral salts and the filtrate was evaporated to dryness under reduced pressure to obtain partially crystallized raw 21-oxalyl derivative which was used as is.

The said product was dissolved in 24 ml of dimethylformamide and 4.3 ml of 1.3 N methanolic potassium hydroxide and after the addition of 2.15 g of potassium acetate thereto, the mixture was cooled to $-5°$ C. Then, a solution of 1.42 g of iodine in 3 ml of tetrahydrofuran and 15 ml of dimethylformamide was added dropwise to the mixture and thereafter, the mixture was stirred at $-5°$ C. for 30 minutes to obtain a suspension which was used as is.

4.3 g of potassium acetate were added to the suspension which was then heated with stirring at 100° C. for 30 minutes and was then cooled. The mixture was diluted with water and was extracted with ethyl acetate. The extract was evaporated to dryness and the residue was chromatographed over silica gel. Elution with a 9-1 benzene-ethyl acetate mixture yielded. 1.170 g of 2,2-dimethyl-13$\beta$-ethyl-21-acetoxy-18,19-dinor-$\Delta^4$-pregnene-3,20-dione melting at 112° C. after crystallization from isopropyl ether.

EXAMPLE 3

2,2-dimethyl-13β-ethyl-18,19-dinor-Δ⁴-pregnene-21-ol-3,20-dione

A solution of 3.4 g of the product of Example 2 in 68 ml of methanol was refluxed under a nitrogen atmosphere for 15 minutes and 840 mg of potassium bicarbonate and 8.4 ml of water were added thereto. Reflux under the nitrogen atmosphere was continued for 30 minutes and then the mixture was cooled and 1 ml of acetic acid was added thereto. The mixture was concentrated under reduced pressure and was then diluted with water and extracted with methylene chloride. The organic phase was washed with water, was dried and evaporated to dryness to obtain 3.06 g of residue. The residue was chromatographed over silica gel and was eluted with a 8–2 benzene-ethyl acetate mixture to obtain 3 g of 2,2-dimethyl-13β-ethyl-18,19-dinor-Δ⁴-pregnene-21-ol-3,20-dione melting at 138° C. after crystallization from aqueous ethanol.

EXAMPLE 4

2,2-dimethyl-13β-ethyl-21-(4-pyridinylcarbonyloxy)-18,19-dinor-Δ⁴-pregnene-3,20-dione A suspension of 541 mg of isonicotinic acid in 25 ml of pyridine and 760 mg of tosyl chloride under an inert atmosphere was stirred at −10° C. for 20 minutes and then 717 mg of the product of Example 3 were added thereto. The mixture was stirred for 90 minutes at 10° C. and was then poured into water. The mixture was made alkaline with an aqueous sodium bicarbonate solution and was extracted with methylene chloride. The organic extracts were washed with aqueous sodium bicarbonate solution, then with water, dried and evaporated to dryness. The residue was chromatographed over silica gel and was eluted with 6–4 benzene-ethyl acetate mixture to obtain 750 mg of 2,2-dimethyl-13β-ethyl-21-(4-pyridinylcarbonyloxy)-18,19-dinor-Δ⁴-pregnene-3,20-dione which melted at 156° C. after crystallization from isopropyl ether.

EXAMPLE 5

Tablets were prepared containing 50 mg of the product of Example 3 and sufficient excipient of talc, starch and magnesium stearate for a final weight of 250 mg.

PHARMACOLOGICAL DATA

A. Antialdosterone activity of the product of Example 3

The study used a test inspired by Kagawa [Proc. Soc. Expt. Biol. Med., Vol. 99 (1958), p. 705] and Marcus [Endocrinology, Vol. 50 (1952), p. 286] wherein male rats of Sprague Dawley SPF IFFA CREDO strain weighing about 180 g were surrenalectomized 7 days before diuresis. The animals were anesthesized with Imalgene (Ketamine) intraperitoneally at a dose of 100 mg/kg. After the operation and just at the end of the experience, the animals received physiological serum as drinking water.

17 hours before the diuresis, the animals were not given any food and the physiological serum was replaced with water containing 5% of glucose. The product of Example 3 was orally administered one hour before placing the rats in a cage and at the start of diuresis, the animals received a hydrosaline surcharge intraperitoneally at a dose of 5 ml per rat of 9% physiological serum and a subcutaneous administration of 1 μg/kg of monoacetate of aldosterone in a 2.5% alcoholic solution.

The rats were then placed by pairs in the diuresis cages without food or water for 4 hours and at this time, emission was forced by pressure on the vessels and the volume of urine collected was measured. After rinsing throughly the cages and the glass walls, the volume of urine was adjusted to 50 ml. Using this solution, the amount of urinary potassium and sodium was determined photometrically in the flame of an autoanalyser. The results were expressed in percent of inhibition of the activity of 1 μg/kg of the monoacetate of aldosterone injected subcutaneously from the log of the ratio of sodium concentration to potassium concentration using the Kagawa Method [Endocrinology, Vol. 67 (1960), p. 125–132]. The product of Example 3 at a dose of 2 mg/kg orally administered showed a clear antialdosteronic activity as the percent of inhibition at this dose was about 60%.

Various modifications of the products and processes of the invention may be made without departing from the spirit or scope thereof and it is to be understood that the invention is intended to be limited only as defined in the appended claims.

We claim:

1. A 19-nor-steroid of the formula

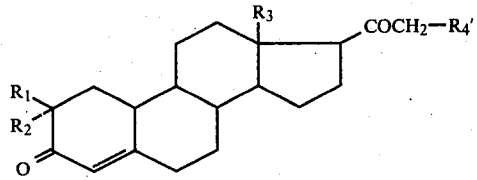

wherein $R_1$ and $R_2$ taken together form a cycloalkyl of 3 to 8 carbon atoms or are individually selected from the group consisting of hydrogen, alkyl of 1 to 4 carbon atoms and alkenyl and alkynyl of 2 to 6 carbon atoms with the proviso that both cannot be hydrogen, $R_3$ is alkyl of 2 to 4 carbon atoms, $R_4'$ is selected from the group consisting of hydrogen, hydroxyl, acyloxy of an organic carboxylic acid of 1 to 18 carbon atoms and

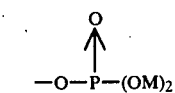

and M is selected from the group consisting of hydrogen and alkali metal.

2. A compound of claim 1 wherein $R_4'$ is selected from the group consisting of hydrogen, —OH and acyloxy of an organic carboxylic acid of 1 to 18 carbon atoms.

3. A compound of claim 1 wherein $R_3$ is ethyl.

4. A compound of claim 1 wherein $R_1$ and $R_2$ are both methyl.

5. A compound of claim 1 of the formula

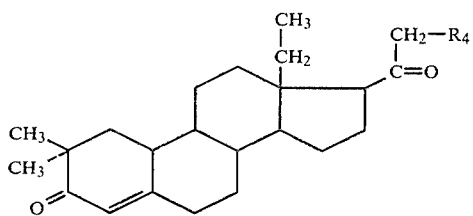

wherein $R_4$ is selected from the group consisting of hydrogen, —OH and acyloxy of an organic carboxylic acid of 1 to 18 carbon atoms.

6. A compound of claim 1 wherein $R_4'$ is hydrogen.
7. A compound of claim 1 wherein $R_4'$ is acetoxy.
8. A compound of claim 1 wherein $R_4'$ is —OH.
9. A compound of claim 1 wherein $R_4'$ is 4-pyridinylcarbonyloxy.
10. A compound of claim 1 which is 2,2-dimethyl-13$\beta$-ethyl-18,19-dinor-$\Delta^4$-pregnene-21-ol-3,20-dione.
11. A composition for the treatment of arterial hypertension and cardiac insufficiency comprising an amount of at least one compound of claim 1 sufficient to relieve cardiac insufficiency and arterial hypertension and an excipient.
12. A composition of claim 11 wherein $R_4'$ is selected from the group consisting of hydrogen, —OH and acyloxy of an organic carboxylic acid of 1 to 18 carbon atoms.
13. A composition of claim 11 wherein $R_3$ is ethyl.
14. A composition of claim 11 wherein $R_1$ and $R_2$ are both methyl.
15. A composition of claim 11 of the formula

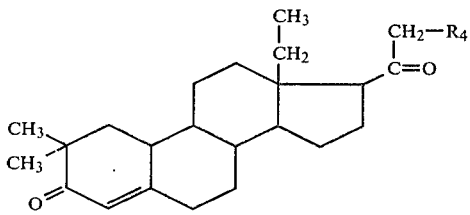

wherein $R_4$ is selected from the group consisting of hydrogen, —OH and acyloxy of an organic carboxylic acid of 1 to 18 carbon atoms.

16. A composition of claim 11 wherein $R_4'$ is hydrogen.
17. A composition of claim 11 wherein $R_4'$ is acetoxy.
18. A composition of claim 11 wherein $R_4'$ is —OH.
19. A composition of claim 11 wherein $R_4'$ is 4-pyridinylcarbonyloxy.
20. A composition of claim 11 wherein the compound is 2,2-dimethyl-13$\beta$-ethyl-18,19-dinor-$\Delta^4$-pregnene-21-ol-3,20-dione.
21. A method of relieving arterial hypertension and cardiac insufficiency in warm-blooded animals comprising administering to warm-blooded animals an amount of at least one compound of claim 1 sufficient to relieve arterial hypertension and cardiac insufficiency.
22. A method of claim 21 wherein $R_4'$ is selected from the group consisting of hydrogen, —OH and acyloxy of an organic carboxylic acid of 1 to 18 carbon atoms.
23. A method of claim 21 wherein $R_3$ is ethyl.
24. A method of claim 21 wherein $R_1$ and $R_2$ are both methyl.
25. A method of claim 21 of the formula

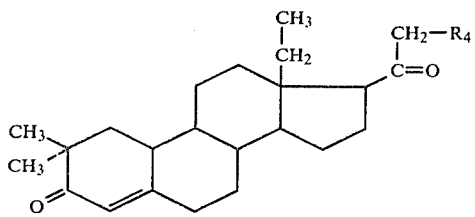

wherein $R_4$ is selected from the group consisting of hydrogen, —OH and acyloxy of an organic carboxylic acid of 1 to 18 carbon atoms.

26. A method of claim 21 wherein $R_4'$ is hydrogen.
27. A method of claim 21 wherein $R_4'$ is acetoxy.
28. A method of claim 21 wherein $R_4'$ is —OH.
29. A method of claim 21 wherein $R_4'$ is 4-pyridinylcarbonyloxy.
30. The method of claim 21 wherein the compound is 2,2-dimethyl-13$\beta$-ethyl-18,19-dinor-$\Delta^4$-pregnene-21-ol-3,20-dione.
31. A process for the preparation of a compound of claim 1 comprising reacting a compound of the formula

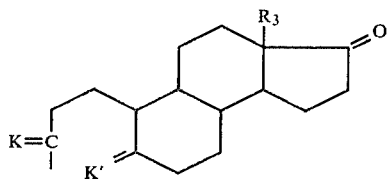

wherein K and K' are ketone blocking ketal groups and $R_3$ is alkyl of 2 to 4 carbon atoms with a triphenyl ethyl phosphonium halide of the formula

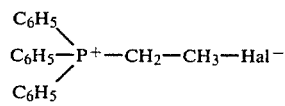

wherein Hal is a halogen in the presence of a strong base to form a compound of the formula

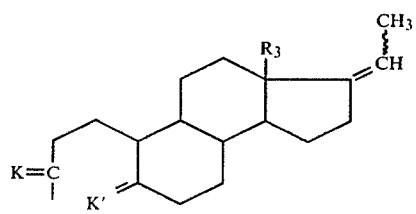

in the form of its cis and trans isomers, optionally separating the said isomers, reacting the compound in the form of its isomer or mixtures thereof with a hydroboration agent, then with an oxidation agent in an alkaline medium, then with a deketalization agent and finally a cyclization agent to obtain a compound of the formula

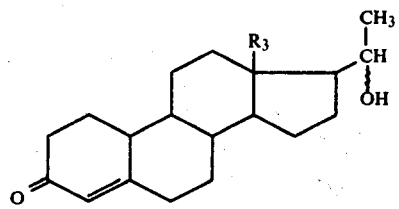

in the form of its 20R or 20S isomers or a mixture thereof, reacting the compound of formula V with an alcohol blocking agent to obtain a compound of the formula

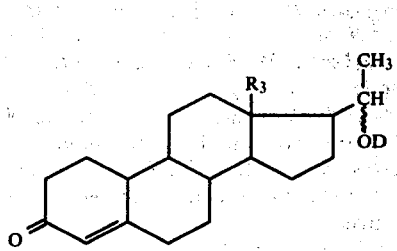

in the form of its 20R or 20S isomer or a mixture thereof and OD is an ether group, reacting the compound of formula VI with an alkyl halide, alkenyl halide or alkylnyl halide in the presence of a basic agent at low temperatures to obtain a compound of the formula

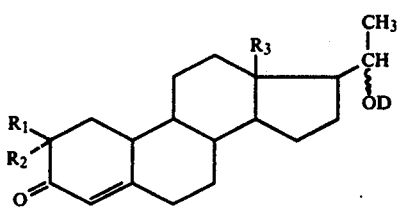

wherein $R_1$ and $R_2$ have the above definition in the form of its 20R or 20S isomer or a mixture thereof, reacting the compound of formula VII with a hydrolysis agent and then an oxidation agent to obtain a compound of the formula

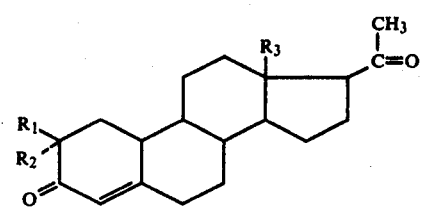

optionally reacting the latter with lead tetraacetate or with an oxalylation agent and then a halogenation agent to form the corresponding 21-halo compound and reacting the latter with an acetoxylation agent to obtain a compound of the formula

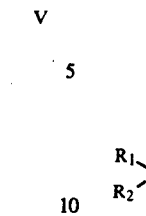

optionally reacting the latter with a saponification agent to obtain a compound of the formula

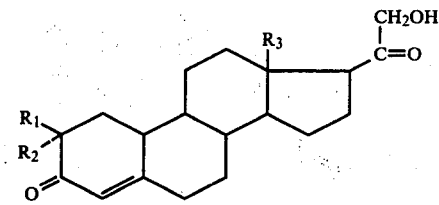

optionally reacting the latter with an organic carboxylic acid of 1 to 18 carbon atoms or a functional derivative thereof to obtain a compound of the formula

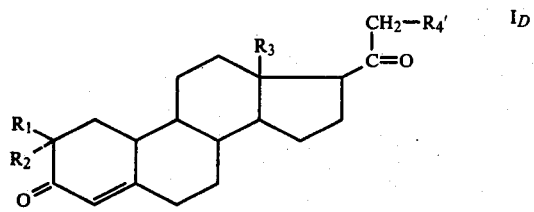

wherein $R_4'$ is an acyloxy of an organic carboxylic acid of 1 to 18 carbon atoms or with a functional derivative of phosphoric acid to obtain the compound of formula $I_D$ wherein $R_4'$ is

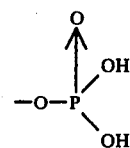

which may be salified, if desired.

32. A compound having a formula selected from the group consisting of

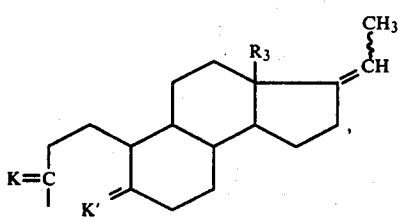

-continued

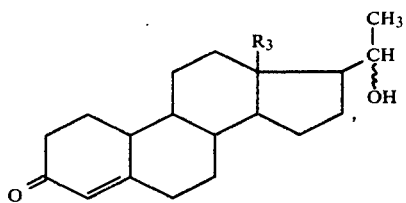

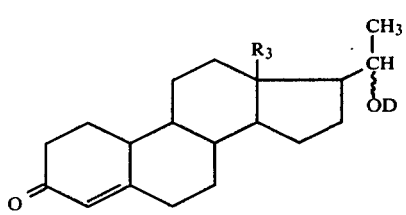

and

-continued

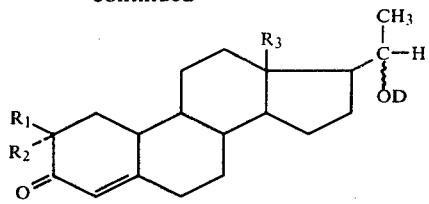

wherein K and K' are ketone blocking ketal groups, $R_3$ is alkyl of 2 to 4 carbon atoms, OD is an ether group and $R_1$ and $R_2$ are hydrogen, alkyl of 1 to 4 carbon atoms, alkenyl and alkynyl of 2 to 6 carbon atoms with the proviso both are not hydrogen and together form cycloalkyl of 3 to 8 carbon atoms.

33. A compound of claim 32 selected from the group consisting of Z and E isomers of bis-(1,2-ethanediyl)-acetal of 13$\beta$-ethyl-18,19-dinor-4,5-seco-$\Delta^{17(20)}$-pregnene-3,5-dione, 13$\beta$-ethyl-18,19-dinor-20-(R,S)-hydroxy-$\Delta^4$-pregnene-3-one, 13$\beta$-ethyl-(2'-R,S-20-R,S)-20-[2'-tetrahydropyranyloxy]-18,19-dinor-$\Delta^4$-pregnene-3-one and (2'R,S-20R,S) 2,2-dimethyl-13$\beta$-ethyl-20-[2'-tetrahydropyranyloxy]-18,19-dinor-$\Delta^4$-pregnene-3-one.

* * * * *

UNITED STATES PATENT AND TRADEMARK OFFICE
CERTIFICATE OF CORRECTION

PATENT NO. :   4,263,290
DATED       :   April 21, 1981
INVENTOR(S) :   LUCIEN NEDELEC ET AL.

It is certified that error appears in the above—identified patent and that said Letters Patent is hereby corrected as shown below:

Column 3, the portion of structural formula IV which reads

" 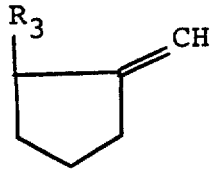 " should read -- 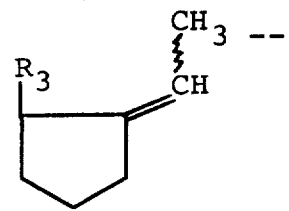 --.

Column 6, line 50: "transuctaneously" should read

-- transcutaneously --.

Signed and Sealed this

Twentieth Day of October 1981

[SEAL]

Attest:

GERALD J. MOSSINGHOFF

Attesting Officer   Commissioner of Patents and Trademarks